United States Patent [19]

Bartholomew et al.

[11] Patent Number: 5,683,592

[45] Date of Patent: Nov. 4, 1997

[54] SURGICAL CUTTING TOOL

[75] Inventors: Richard Shiayle Bartholomew, Mid Calder; Graham John Ensell, Salisbury; Shih Jung Eric Yang, Balerno, all of England

[73] Assignee: British Technology Group Limited, London, England

[21] Appl. No.: 505,246

[22] PCT Filed: Feb. 25, 1994

[86] PCT No.: PCT/GB94/00380

§ 371 Date: Aug. 15, 1995

§ 102(e) Date: Aug. 15, 1995

[87] PCT Pub. No.: WO94/18920

PCT Pub. Date: Sep. 1, 1994

[30] Foreign Application Priority Data

Feb. 26, 1993 [GB] United Kingdom .................. 9303985

[51] Int. Cl.[6] .................................................. B44C 1/22
[52] U.S. Cl. ........................ 216/24; 216/41; 216/96; 606/166
[58] Field of Search ............................. 606/166; 216/2, 216/11, 24, 41, 56, 96, 97; 156/657.1

[56] References Cited

U.S. PATENT DOCUMENTS

| 3,926,601 | 12/1975 | Hicks ........................................ 216/97 |
| 4,968,585 | 11/1990 | Albrecht et al. . |
| 5,156,607 | 10/1992 | Kansas . |
| 5,248,383 | 9/1993 | Hanada ..................................... 216/41 |
| 5,302,234 | 4/1994 | Grace et al. ............................. 216/47 |

FOREIGN PATENT DOCUMENTS

| 2588751 | 4/1987 | France . |
| 3618768 | 8/1987 | Germany . |
| 4 83887 | 3/1992 | Japan . |
| 3103400 | 4/1994 | Japan . |
| 989082 | 4/1965 | United Kingdom . |
| 2227362 | 7/1990 | United Kingdom . |

OTHER PUBLICATIONS

"Micromachined silicon surgical tool", Machine Design, vol. 62, No. 23, Nov. 1990, p. 32, XP000176637.

*Primary Examiner*—William Powell
*Attorney, Agent, or Firm*—Cushman, Darby & Cushman IP Group of Pillsbury Madison & Sutro LLP

[57] ABSTRACT

This invention concerns a method of fabricating a surgical cutting tool and a tool fabricated by such method. The surgical cutting tool (20) comprises a base (21) and an upstanding cutting blade (22), fabricated by locating a mask (32) of a shape corresponding to that of the required cutting blade on the surface of a substrate (31) and etching the substrate from its exposed surface and undercutting the mask from the edges thereof to thereby for a cutting edge of an upstanding cutting blade (22) in the substrate under at least a part of the mask. The tool of the invention is particularly suitable for cutting thin membranes within the human or animal body and has specific application in extracapsular cataract extraction operations, where accurate cutting of the thin membrane of the eye's lens capsule is required.

17 Claims, 4 Drawing Sheets

SURGICAL CUTTING TOOL

This invention concerns a method of fabricating a surgical cutting tool and a tool fabricated by such a method. More particularly, the tool of the invention is intended for accurate cutting of thin membranes within the human or animal body. The invention has particular application in eye surgery, and more specifically in cataract surgery, which requires cutting of the thin membrane of the eye's lens capsule.

Cataract accounts for more than half of all eye operations in western countries and the number of operations carried out is increasing with, among other things, the increase in life expectancy.

Cataract is defined as an opacity of the crystalline lens of the eye. It may be hereditary, i.e. passed on genetically from one generation to the next. It may be present due to infection of the patient's mother during pregnancy, and typically rubella can cause cataracts in this way. Certain congenital syndromes are associated with cataracts, e.g. Down's syndrome. Cataract may be acquired later in life from injury (either directly or indirectly from trauma or radiation), from disease, such as diabetes, from eye disease, such as uveitis, acute glaucoma, retinitis pigmentosa, or as a result of using certain drugs, such as steroids. Most commonly cataract is associated with the ageing process, akin to the whitening of hair or the ageing of skin. Changes occur within the lens of an otherwise perfectly healthy eye which render the lens gradually opaque. The changes include lens protein aggregation, increased amounts of insoluble lens protein and increased pigmentation of the lens nucleus.

The result of cataract is progressive deterioration in vision. The patient experiences initial blurring, glare, double or multiple images, then increasing loss of visual acuity and finally almost total blindness, although perception of light is retained. Such visual loss has a significant effect upon the development and education of neonates and children and the ability of adults to perform or continue with many functions including some, such as driving a motor car, upon which their livelihood may depend.

In later life such ability is a major factor determining whether such a person can continue to live an independent life.

At present, no satisfactory medical treatment for cataract and no effective methods of prevention have been found. The only treatment is the surgical removal of the lens, and such surgery is long-established and has a good rate of success.

The two common forms of cataract extraction are intracapsular and extracapsular extraction. In the first of these the zonule is dissolved with chymotripsin (an enzyme) and the whole lens (capsule, cortex and nucleus) is removed by means of a cryoprobe. This method was the more common until a number of years ago, but has now been replaced by that of extracapsular extraction, in which a small hole is made in the anterior lens capsule and the cortex and the nucleus are removed through this hole leaving the posterior part of the lens capsule in place.

Having had a cataract removed the eye is made long-sighted and an alternative means of focusing light on the retina must be found. The alternatives are cataract glasses, contact lenses or a perspex implant Known as an intra-ocular lens (IOL). The first two alternatives, though being very safe options from the point of view of biocompatability, suffer from major functional limitations. Spectacle lenses are located about 17 mm in front of the position of the crystalline lens which they replace. In this position a very high-magnification lens is needed resulting in a reduced field of view and an unnatural image magnification. When the latter condition exists unilaterally, stereoptic fusion, the blending of perceived images from the two eyes, becomes impossible.

Contact lenses do not present this problem since their image magnification is not required to be so high. However, their manipulation and placement presents practical disadvantages and, in the case of the elderly who make up the majority of the patients, it can be almost impossible to manage the tasks associated with care of daily-wear lenses adequately. Although extended-wear contact lenses are now available, such lenses are not free of problems and are certainly not suitable in the case of more than a small fraction of the total number of cataract patients.

The IOL is therefore the most popular means of vision restoration in cataract patients and increasingly sophisticated implants have been developed and successfully utilised since the first of such operations were carried out. The IOL consists of two major parts: the optical element, known as the optic, and the supporting members, Known as haptics. The optic can be biconvex, convex-planar or convex-concave in shape. The IOL can be fitted into the anterior chamber of the eye (between the cornea and the iris base), into the iris support (by placing the optic directly on one side of the iris and fixing the haptics to the other side of the iris), or into the posterior chamber (by approximating the position of the crystalline lens). In the latter location, the haptics can be fitted into the ciliary body supporting the lens capsule or preferably inside the capsule itself. This is the most popular location for the IOL but relies on the integrity of the lens capsule found after extracapsular cataract extraction.

At present, cataract surgery has a success rate of 90–95%, signifying the percentage of patients with some restoration of vision. However, failures of only 5% are very significant because of the large number of operations involved.

Successful and accurate removal of the central 4–7 mm of the anterior capsule is the key to a successful extracapsular extraction cataract operation.

At present, this is done by a multiple puncture and scraping or tearing technique, in which the surgeon uses a sharp instrument, akin to a needle with a serrated tip, to puncture a ring of holes of the required diameter in the anterior capsule, concentric with the centre of the natural lens. He then uses the tip of the instrument to tear out the disc of material within this ring so that it can be removed. This 'free-hand' technique leaves the edges of the circular aperture in a ragged state such that subsequent manipulation to remove the lens cortex and nucleus and then to insert the IOL can very easily tear the remaining anterior capsule material to the periphery of the capsule and around the equator to involve the posterior layers of the capsule. In this case the stability of the IOL location will be jeopardised and the operation can be a failure, or the implant can fail at a later date.

A trepanning tool designed for extracapsular cataract extraction is disclosed in Patent Application FR 2588751. This consists of a circular blade with a cutting edge connected to a hollow conduit for supplying irrigation or other fluid, the cutting edge of the tool being pressed against the anterior lens capsule and slightly rotated to effect cutting of the capsule. No method for manufacturing the blade of the tool is described.

The prior art for the purposes of the present application also includes Patent Application JP- A- 4 083 887 (and the equivalent abstract published in Week 9217, Derwent Publications Limited, AN-138998), and Patent DE-C-36 18 768.

These disclose methods of preparation of jutting blades on steel plates for the purposes of fabricating trimming and stamping dies. The methods described involve etching by etchants such as ferric chloride, making use of applied resist-films corresponding to the desired form of the cutting blade.

It is an object of the present invention to eliminate the disadvantages described above in current practice and to this end there is provided a method of fabricating a surgical cutting tool comprising a base and an upstanding cutting blade of non-metallic material, said method comprising the steps of:

locating a mask of a shape corresponding to that of the required cutting blade on a surface of a non-metallic substrate, and etching the substrate from its exposed surface and undercutting the mask from the edges thereof to thereby form a cutting edge of an upstanding cutting blade in the substrate under at least a part of the mask.

Preferably, the mask is located on the substrate surface by photolithographic etching of a layer of inorganic material such as aluminium, silicon dioxide or silicon nitride previously applied to the surface. Alternatively the mask may be deposited on the substrate surface.

The non-metallic material of the substrate is preferably silicon. It is a relatively low-cost material for which etching technology has been widely developed with respect to the electronics industry, and furthermore it is a suitable material from the point of view of biocompatibility.

It is particularly suitable for producing cutting tools according to the invention of single use, disposable form. An alternative appropriate material is quartz.

The shape of the cutting tool produced by the method of the invention depends on the shape of the mask, which may be circular annular, elliptical annular, triangular, rectangular, or any other suitable form. The mask is preferably supported during etching by support elements, and in one detail of the invention these support elements are sized and arranged such that the etching process produces a serrated cutting blade of the form required.

To produce a cutting blade which is sufficiently deep and as sharp as possible, the etching preferably comprises a two-stage process. The first stage is wet etching in a suitable known acid solution, followed by a second stage of dry (gas plasma) etching.

The surgical cutting tool of the invention features an accurately machined hard cutter blade of very high sharpness, which can be manufactured in bulk and is consequently inexpensive. In use in cataract surgery the cutting tool allows a much more reliable capsulotomy operation than currently possible. A clean cut with a smooth edge can be consistently produced, thus reducing the failure rate for such operations. The aperture thus produced is very much less likely to tear on stretching, and indeed considerable deformation will be possible during removal of the nucleus and cortex and insertion of the implant. Fewer remnants will be left in the eye to be removed as part of the operation. Moreover a smaller aperture can be cut in the lens capsule than was hitherto practicable, the edges being pulled back to allow the operation to proceed. When the IOL is implanted, the edges can be released to aid in stabilisation.

Considerable time-saving results from the use of this cutting tool in the cataract operation, reducing the overall cost of such surgery.

Certain embodiments of the invention will now be described by way of example with reference to the accompanying drawings, in which.

Figure 1:
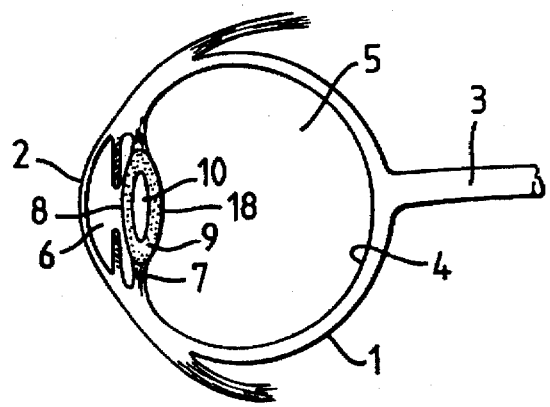
FIG. 1 illustrates in an idealised form an anterioposterior cross-section of the eye.

In FIG. 1 a schematic cross-section of the eye is shown. Though greatly simplified, it illustrates the main components of the eye, including the sclera 1, the cornea 2, the optic nerve 3, the retina 4, the posterior chamber 5, the anterior chamber 6, the ciliary body and zonules 7, the lens capsule 8,18, the lens cortex 9 and the lens nucleus 10. The optical system in the eye is composed of two lens elements: the cornea 2, which is of multilayer form, and the crystalline lens comprising component parts 8,9,10,18. Each lens element contributes to image focusing on the sensory tissue, the retina 4.

The crystalline lens provides refraction and optical function by its biconvex shape, high light transmittance, and flexible lamellar structure. The lens capsule comprises anterior and posterior portions 8 and 18 that enclose the outer cortex layers 9 and a harder central nucleus 10. The lens is held at its equator by fibrous zonules 7 which attach to the ciliary body and suspend the crystalline lens within the eye. The variable focus of the eye is supplied by contraction and relaxation of the ciliary body, which causes the flexible lens to change shape. This process, called accommodation, diminishes with age as the crystalline lens becomes less flexible.

Figure 2A:
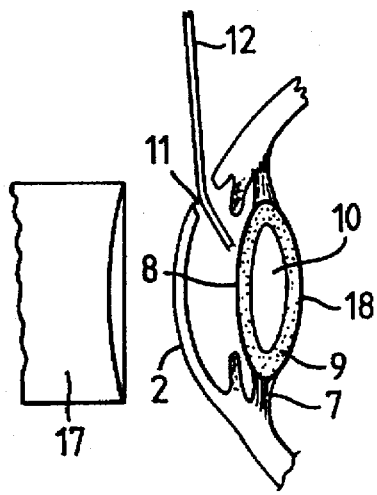
FIGS. 2a to 2c illustrate the lens and the successive stages of its removal and replacement with an IOL in a traditional cataract operation.
Figure 2B:
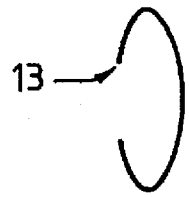
Figure 2C:
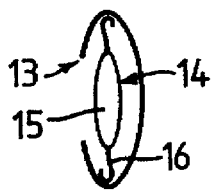

FIGS. 2a–2c show the steps of the extracapsular cataract extraction as currently performed. Initially an opening 11 is surgically cut with a scalpel in the upper anterior part of the cornea 2, out of the patient's sight line. This incision may typically be of about 6 mm in length. The surgeon then introduces a cutting tool 12 (FIG. 2a), which comprises a shaped needle with a lumen through which irrigation fluid can be passed, which he uses to cut a circular aperture 4–7 mm in diameter in the anterior capsule 8, retaining the necessary ⅚th of the capsule which can subsequently be used for short- and long-term fixation and stabilisation of the implant, necessary for satisfactory optical result.

The cataract is now removed from the capsule. The hard nucleus and soft cortex is mechanically extracted through the circular aperture with cortical remnants evacuated by the combination of irrigation with a saline solution and simultaneous aspiration. Alternatively the technique of phacoemulsification can be employed, the lens being first fragmented by means of an ultrasonic probe and the fragmented remnants being removed by irrigation and aspiration. In both cases, of course, care must be taken not to tear the layers of the capsule. The result of the extraction is shown in FIG. 2b, the aperture being indicated by reference 13.

The artificial IOL 14 is then introduced through the capsule aperture 13 (FIG. 2c). It consists of an optic 15 and supporting haptics 16, the latter being placed to rest against the inner surface of the equator of the capsule.

No attempt is made to close up the capsule opening 13 after the IOL has been implanted. The opening in the cornea is stitched up and the eye covered overnight whilst healing begins. Complete healing takes about three months. The operation is performed under local or general anaesthetic and a simple microscope 17 (FIG. 2a) is placed in front of the cornea to assist the surgeon in carrying out the operation.

As already explained, the key to the cataract operation is accurate cutting and removal of the central part of the anterior capsule, an operation known as a capsulotomy. If the capsule tears then the posterior contents of the eyeball can prolapse forward, and the implant may not be held sufficiently in position or may undergo late displacement, compromising a good visual result. At present the cutting tool 12, which may feature a serrated tip to aid cutting, is used to puncture a ring of small holes, about 25 in number. The surgeon then has to manipulate the tool to scrape and tear out the circle of capsule material within this ring. The process is slow and produces inconsistent results, and in most cases leaves a ragged edge to the circular aperture 13. Any stretching of the capsule upon later manipulation to remove the natural lens or to implant the IOL may then cause the edge of the capsule to tear from the centre to the periphery and beyond, with the undesired results already described. Additionally the barrier provided by the posterior capsule between the anterior and posterior chambers of the eye, which can reduce other post-operative complications, will lose its integrity.

It is extremely difficult to produce free-hand a capsulotomy with an edge such that this risk of tearing is satisfactorily reduced.

Figure 3:
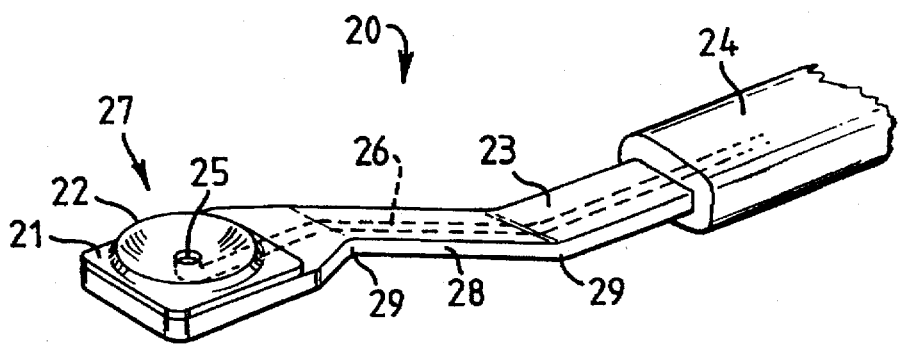
FIG. 3 illustrates a cutting tool according to the present invention for realising a hole in the anterior lens capsule.

FIG. 3 illustrates in isometric view a cutting tool 20 according to the invention for use in a capsulotomy. A cutter 27 comprises a thin silicon base 21 with a raised circular cutter blade 22, the cutter blade being produced by etching by means of a technique described below. The silicon base 21 has a planar back surface which is mounted on the end of a support strip 23 of stainless steel, the back surface of the base being secured to the face of the strip by adhesive or otherwise. The other end of the strip 23 is connected to a handle 24 by which the surgeon can hold and manoeuvre the cutting tool. In FIG. 3 a circular aperture 25 is shown in the centre of the silicon base 21, concentric with the cutter blade 22. This is not a necessary feature of the tool but may be included to form a port by which irrigation or other fluid can be introduced to the operation site, or material and fluid can be aspirated from the operation site. For this purpose a longitudinal lumen 26 can be provided running along the length of the support strip 23 to provide a conduit connecting with this aperture 25.

It is to be noted that the silicon base 21 is shown as a rectangular slice, but may of course be a circular disc or any other shape. Similarly the strip 23 may be of any suitable cross-section, such as circular or elliptoid. A flattened strip is preferred because it provides a convenient mounting surface for the silicon base 21 and has the advantage of adequate stiffness in bending about the neutral axis perpendicular to the surface of the strip, which is useful for successful manoeuvring of the cutting-tool 20 as will be appreciated from the description of the operation below. The support strip 23 is dimensioned and shaped to allow it to be manoeuvred as easily as possible within the eye, and for this purpose the strip shown in FIG. 3 features a narrowed portion 28 between the handle 24 and the cutter 27, and two spaced opposed bends 29 of equal angle.

The use of this cutting tool is very simple. The surgeon introduces the cutter 27 on the support strip 23 through the corneal aperture, with the cutter blade 22 directed posteriorly. He manoeuvres it, with the assistance of microscope 17, such that the cutter blade 22 is concentric with the centre of the lens, and then exerts pressure to push the cutter blade against the capsule. The sharpness of the blade means that a slight pressure is all that should be needed to realise a smooth edge capsulotomy. Should it be necessary, a few degrees of turning movement about the centre of the circular cutter blade can be exerted by the surgeon and the support strip 23 is sufficiently stiff in this direction to permit this. The disc of capsule material can then be easily extracted and the IOL inserted, With a smooth edge the annular aperture remaining will tear less readily on stretching, and indeed, considerable deformation is possible during the subsequent stages of the operation. As a result, fixation for the implant and long-term centration and stabilisation are excellent.

With this method of capsulotomy, an aperture considerably smaller than that necessary with present techniques can be cut, since the edges of the aperture can be safely stretched by suitable means to insert an IOL of larger dimensions before releasing the edges to close over the implant.

The capsule of a normal human eye is approximately 20 μm in thickness, so a cutting blade of greater depth, typically of 40–100 μm from tip to base, is sufficient to realise the aperture.

FIGS. 4a–d represent the process sequence for fabricating the silicon cutter 27. The desired form is achieved by selective etching to obtain the desired structural characteristics, and a description of an appropriate etching process is given below by way of example.

Figure 4A:
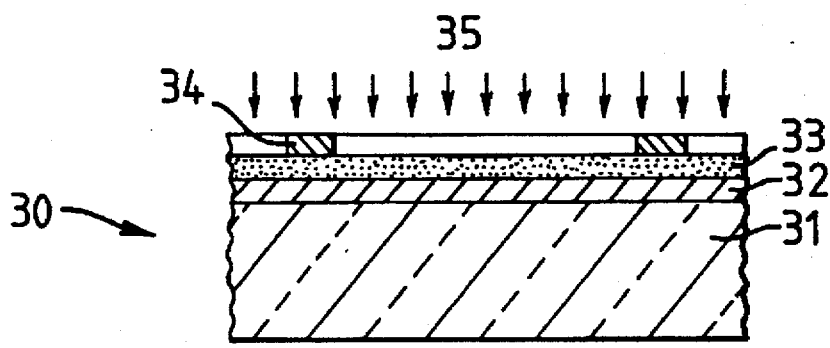
FIGS. 4a to 4d illustrate the successive steps in a method according to the invention of fabricating a cutting tool as shown in FIG. 3.
Figure 4B:
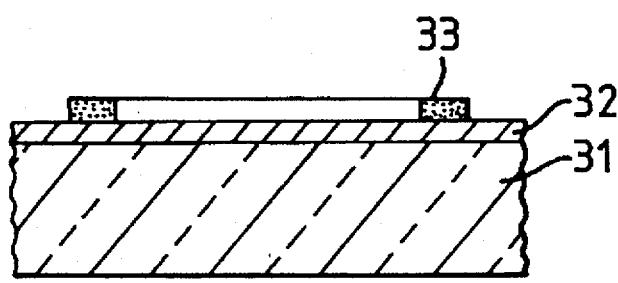

The cutter is preferably made as one of a batch of such cutters on a single wafer 30 which can then be cut down to separate the individual elements. Firstly a layer of $SiO_2$ 32 of 0.5–1.5 μm in thickness is grown or deposited on the surface of single-crystal silicon substrate 31. A positive photo-resist layer 33 is then spun at 2000 rpm over the surface of the $SiO_2$ layer and baked at 95° C. to drive off solvents in the resist before a photographic mask 34 is positioned over the photoresist 33, the mask shape including an annulus corresponding in shape to the required cutting blade. The photoresist layer thickness is typically 1.0–2.5 μm depending on viscosity and spin speed. The wafer is then exposed to ultraviolet light 35 through the mask 34 (FIG. 4a) and the photo-resist is developed, the exposed regions being removed in the developing stage. The result is shown in FIG. 4b, an annulus of photo-resist 33 remaining as a mask on the $SiO_2$ layer 32. After exposure and development the resist is baked at 115° C. to harden it.

The $SiO_2$ layer 32 is then isotropically etched through the photo-resist mask 33, the etching being carried out at 25° C. in a 7:1 buffered hydrofluoric acid solution. Alternatively, the oxide layer can be isotropically or anisotropically etched in a dry etcher using a fluorinated plasma such as $CHF_3$. The wafer is then cleaned to remove the photo-resist by cleaning in a solvent such as acetone, or in a dry etcher containing an oxygen plasma, or by dissolving in an acid such as fuming nitric acid. This leaves an annular mask of $SiO_2$ on the surface of the silicon wafer 31.

Figure 4C:
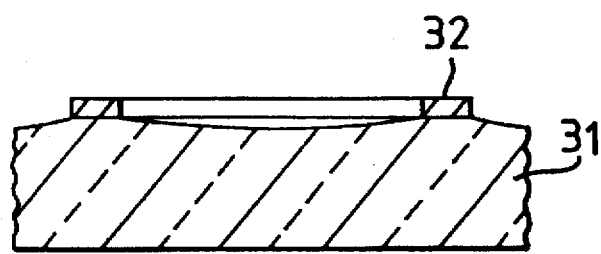
Figure 4D:
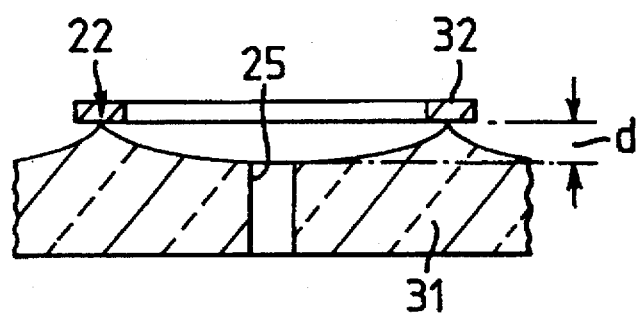

A final etching step is now carried out, a silicon etchant being used to etch the silicon 31 below the $SiO_2$ mask 32 (FIG. 4c). As an example, a dry etch using $SF_6$ plasma at a pressure of 200 millitorr is appropriate. This etching process results in undercutting of the silicon from the edges of the $SiO_2$ mask to form a sharp edge 22 where the undercut surfaces meet below the mask, at which point the etching is terminated (FIG. 4d) and the mask 32 can be removed. This produces an extremely sharp blade 22 in a circle as desired, with a cutter depth d from tip to base as shown in the figure.

If it is desired to produce a port 25 through the cutter 27 for irrigation purposes or otherwise (FIG. 4d), this can be done by masking and etching from the planar backsurface of the silicon slice, either before, at the same time, or after the cutting blade is etched. This port 25 may alternatively be of use as a visual aid in positioning the cutter blade 22 accurately over the lens, for which purpose the port will continue through the support strip 23 or the latter will be provided with a transparent portion where the cutter 27 is supported. Alternatively, the whole area of the base can be separately etched or machined to leave the circular upstanding blade around a circular aperture, this cutter then being attached to the support strip 23.

The silicon coating which constitutes the mask used in the silicon etching process need not be $SiO_2$. For example, $Si_3N_4$ can be used, or a metal coating such as aluminium. If aluminium is used, the mask is formed by etching the aluminium layer at 40° C. with an etchant containing orthophosphoric acid. Alternatively the aluminium layer can be etched either isotropically or anisotropically in a dry etcher using a chlorinated plasma.

Figure 5A:
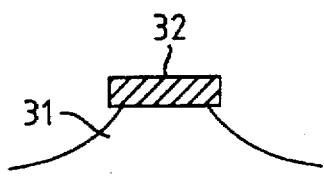
FIGS. 5a to 5d illustrate details of the fabrication process.
Figure 5B:
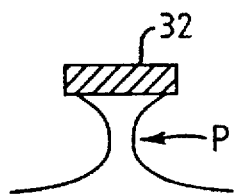
Figures 5C, 5D:
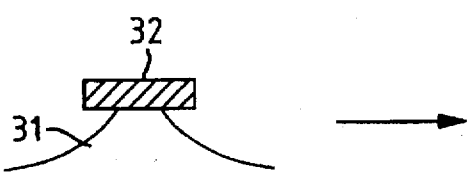

The substrate etching step is the most critical as it is this process which determines the sharpness and depth of the cutter blade 22. Different etching processes produce different degrees of undercutting as illustrated in FIGS. 5a–5d. Wet etching, using an $HF:HNO_3:H_2O$ or $HF:HNO_3:CH_3COOH$ etch will tend to produce a shallow cutter (FIG. 5a), whereas dry etching, using gas plasma, such as $SF_6$ plasma, as an etchant, tends to produce too much undercutting, as shown in FIG. 5b. In this case the undercutting can be such that the substrate necks at a point P at a distance below the base of the mask 32, this again producing a shallow cutter. Ideally a combination of the two etching processes is required, the steps being wet etching, until the section illustrated in FIG. 5c is obtained, followed by a dry etch to achieve a form as illustrated in FIG. 5d. The shorter dry etch step reduces the possibility of unwanted undercutting taking place. This combined process also reduces the processing time and consequently the costs involved.

As an example of the combined wet and dry etch process, a mask is used which is a combination of $SiO_2$ and $Si_3N_4$. Typically a layer of 600 nm of thermally grown $SiO_2$ covered with 160 nm of deposited $Si_3N_4$ is used. Photolithography is carried out as already described, the nitride and oxide layers being wet etched, or dry etched in a fluorinated plasma.

The preferred silicon etchant consists of a mixture of $HF:HNO_3:H_2O$ or $HF:HNO_3:CH_3COOH$, the bulk of the silicon being removed by this etch. The silicon etching is then completed in a $SF_6$ plasma etch. The nitride and oxide layers are subsequently removed by stripping in hot orthophosphoric acid and buffered hydrofluoric acid respectively.

The fabrication technique as described above produces a very accurately formed cutter, although there may be slight variations in the depth d of the cutter around the circumference of the cutter blade. It is thought that a variation in cutter depth of ±10% is quite acceptable and may even aid in the effectiveness of the cutter when it is pressed against the lens capsule, especially if cutting is effected by means of a slight rotation of the tool.

Figure 6A:
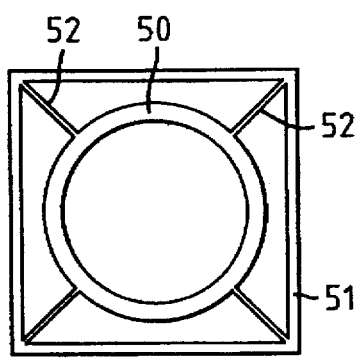
FIGS. 6a to 6c illustrate examples of etching masks which may be used in the method according to the invention.

FIGS. 6 a–c illustrate different masks which can be used the photolithographic technique described above. FIG. 6a shows a mask suitable for producing the circular cutter blade 22 as shown in FIG. 3, the circular annulus 50 being suspended within a square frame 51 by thin straight diagonal ligaments 52 extending from the corners of the square frame to the most adjacent points on the annulus 50. This provides support for the $SiO_2$ annular mask during the silicon etching stage so that does not drop away as the etching takes place. The annular mask may have a diameter of 4.2 mm and an annular radial thickness say, 60 µm. The supporting ligaments will be thinner, so that the substrate below is almost completely removed.

Figure 6B:
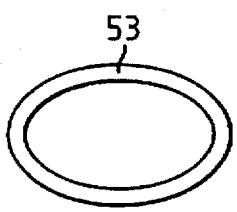

FIG. 6b shows an elliptical annular mask 53, this time without any surrounding supporting structure. Use of this mask will produce a cutter blade with an elliptical shape, and further reference will be made to the use of this cutter below.

Figure 6C:
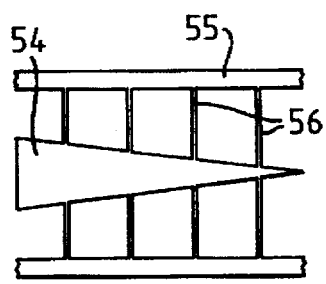

FIG. 6c shows a mask designed to produce a rectilinear cutter blade with its edge inclined to the surface of the base. A narrow wedge-shaped element 54 is suspended from an outer frame 55 by multiple lateral spaced supporting ligaments 56.

A straight rectilinear cutter blade is also envisaged, the mask for this (not shown) being generally of rectangular form and the substrate being etched evenly from opposing longer edges of the rectangular mask until the etched surfaces meet along the longitudinal centre line to form the cutter blade.

Figure 7A:
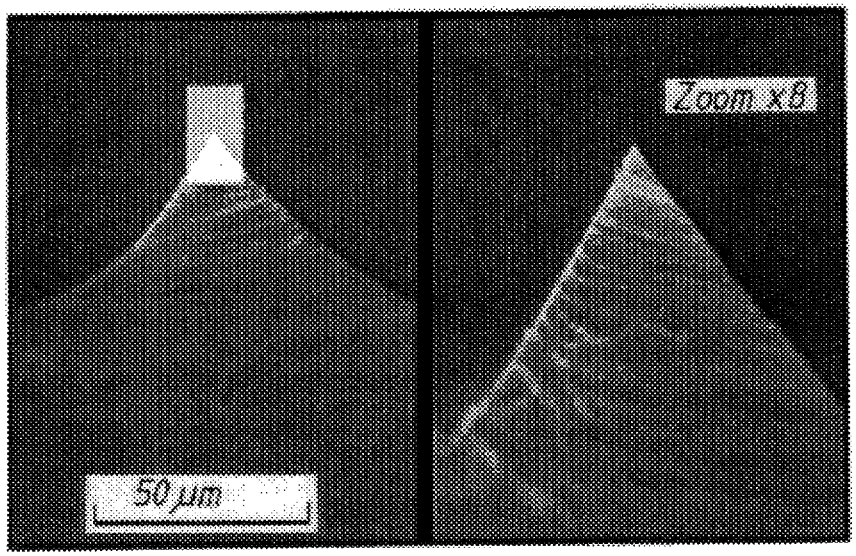
FIGS. 7a to 7c show photographs of the results of etching processes.
Figure 7B:
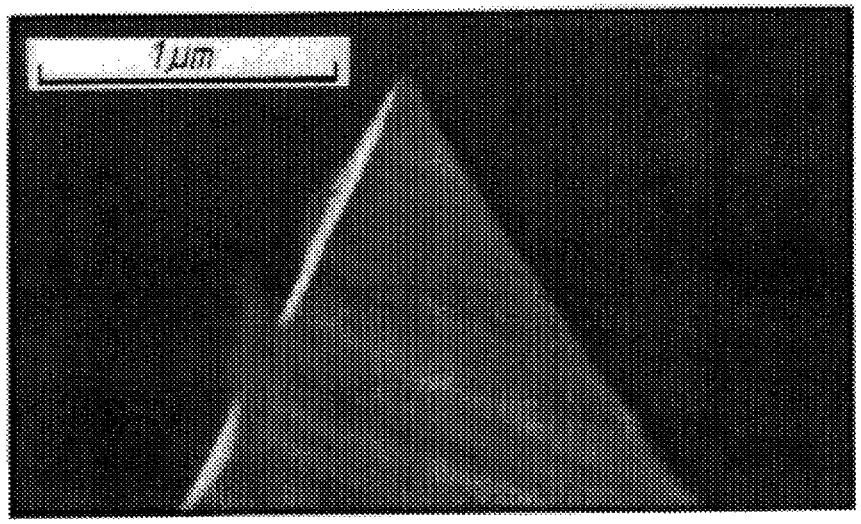
Figure 7C:
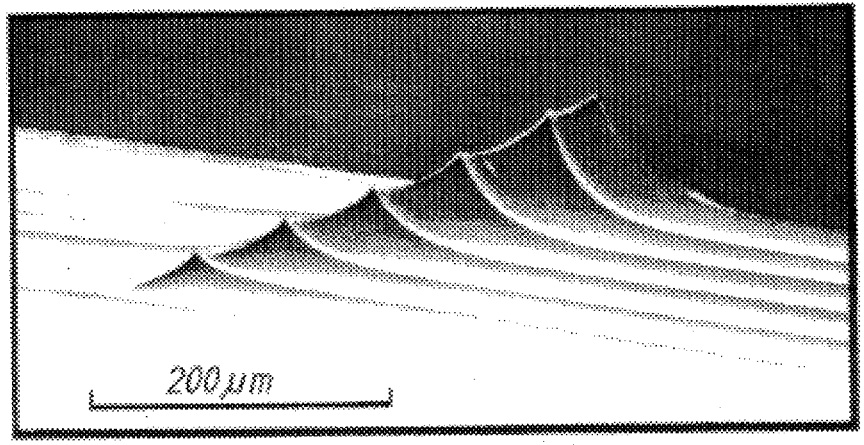

FIG. 7 shows photographs of the cutters produced by the method according to the invention. Two cross-sections of the circular cutter at different magnifications are shown in FIG. 7a, with a further magnified view appearing in FIG. 7b showing the cutting edge of the blade with a radius of less than 40 nm. FIG. 7c shows the inclined rectilinear cutter produced by etching using the mask shown in FIG. 6c. The lateral ridges clearly shown in the photograph are a result of etching below the supporting ligaments 56, and the effect is to produce a blade with a serrated edge inclined to the base. Such a blade may find application in optical surgery where steel or diamond scalpel blades are traditionally used, for example, in surgery of the cornea and in glaucoma surgery, as well as in other stages in the cataract procedure.

A circular annular mask such as that shown in FIG. 6 may be arranged with a plurality of members, such as supporting ligaments, extending radially inwardly and outwardly from the annulus. In etching, use of such a mask will produce a circular serrated cutter which is particularly suitable for producing an effective cutting action when the circular blade is rotated during the operation.

Figure 8:
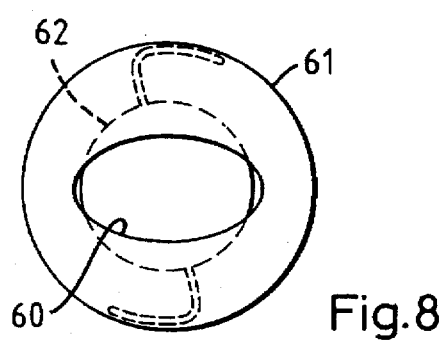
FIG. 8 illustrates a capsule into which an IOL has been inserted.

FIG. 8 represents the use of an elliptical cutter produced using the mask illustrated in FIG. 6b. The cutter produced has an elliptical shape of dimensions 6.5 mm by 4.4 mm and the elliptical aperture 60 that this blade cuts in the lens capsule 61 allows more reliable retention of the IOL 62 after insertion through the aperture.

It has been suggested that the cutter 27, the support strip 23, and the handle 24 are all fabricated separately and then assembled to form the complete cutting tool 20. Alternatively, it is possible to fabricate the whole tool or at east two of these components monolithically. For example, the support strip and cutter may be monolithically etched, a final etching stage being used to produce the desired thickness of the support strip.

The tool described above is fabricated from a surgically acceptable non-metallic material and silicon is a preferred material, although other semiconductor materials may be used. Silicon etching techniques have been widely developed for micro-electronic chip manufacture and other microengineering applications, and single-crystal silicon wafers with a very high degree of crystallographic perfection are readily available at low cost.

Alternatively, the cutter may be made from quartz, as this is also a material appropriate for the two-stage etching process preferred. The quartz cutter would be made as one of a batch on a single quartz wafer and then separated into individual elements. The preferred process is to deposit $Si_3N_4$ and then to deposit and pattern a photo-resist layer in a way identical to the process used on silicon substrates. The nitride is then etched in a plasma etcher to produce a mask, before the quartz is isotropically etched in hydrofluoric acid to produce a cutter section similar to that represented in FIG. 5c. The final etch step is done in a dry etcher using a fluorinated plasma to produce the sharp cutting edge. The nitride is removed in orthophosphonic acid. Alternatively, the process can be carried out with a resist mark only, the $Si_3N_4$ being omitted.

The quartz tool has the advantage of being transparent, facilitating location of the cutter during use. Both silicon and quartz are relatively brittle materials and are very seldom used in surgical tool manufacture. However, the disposable, single use nature of the device of the invention make them ideal materials for this application.

Embodiments of the invention illustrated in the accompanying figures and described above, are given by way of example only, and it should be understood that these in no way limit the scope of the invention which is intended to embrace all embodiments that fall within the spirit and scope of the appended claims.

We claim:

1. A method of fabricating a surgical cutting tool comprising a base and an upstanding cutting blade of non-metallic material, said method comprising the steps of:

locating a mask of a shape corresponding to that of the required cutting blade on a surface of a non-metallic substrate, and etching the substrate from its exposed surface and undercutting the mask from the edges thereof to thereby form a curing edge of an upstanding curing blade in the substrate under at least a part of the mask.

2. A method according to claim 1, whereby said mask is located on said surface of the substrate by etching a layer of inorganic material previously applied to said surface.

3. A method according to claim 2, whereby said layer of inorganic material is etched photolithographically.

4. A method according to claim 2, in which the inorganic material is selected from the group consisting of aluminium, silicon dioxide, silicon nitride and any combination of these three materials.

5. A method according to claim 1, in which the substrate is a silicon wafer.

6. A method according claim 1, in which the substrate is a quartz wafer.

7. A method according to claim 1, in which the part of the mask under which the cutting blade is formed is of generally circular annular form.

8. A method according to claim 1, in which the part of the mask under which the cutting blade is formed is of generally elliptical annular form.

9. A method according to claim 1, in which the part of the mask under which the cutting blade is formed is of generally triangular form.

10. A method according to claim 1, in which the part of the mask under which the cutting blade is formed is of generally rectangular form.

11. A method according to claim 1, in which the mask is shaped such that the etching process produces a serrated upstanding cutting blade.

12. A method according to claim 1, in which the mask comprises support elements which support the part of the mask under which the cutting blade is formed.

13. A method according to claim 1, in which the step of etching the substrate comprises a first stage of wet etching and a subsequent stage of dry plasma etching.

14. A method according to claim 1, in which further etching is carried out to produce an aperture through the base of the cutting tool.

15. A method according to claim 1, in which further etching is carried out to produce a support member for the cutting tool, by which the tool may be manipulated.

16. A surgical cutting tool fabricated by the method of claim 1.

17. A tool according to claim 16 comprising a substantially circular cutting blade suitable for use in cutting the membrane of an eye lens capsule.

* * * * *